(12) United States Patent
Zhu (10) Patent No.: US 7,053,158 B2
(45) Date of Patent: May 30, 2006

(54) CARBORANE TRIANION BASED CATALYST

(75) Inventor: Yinghuai Zhu, Ayer Rajah Crescent (SG)

(73) Assignee: Agency for Science, Technology and Research (SG)

( * ) Notice: Subject to any disclaimer, the term of this patent is extended or adjusted under 35 U.S.C. 154(b) by 138 days.

(21) Appl. No.: 10/668,850

(22) Filed: Sep. 22, 2003

(65) Prior Publication Data

US 2005/0065299 A1    Mar. 24, 2005

(51) Int. Cl.
*C08F 4/60* (2006.01)
*C07F 5/02* (2006.01)
*C07F 5/05* (2006.01)

(52) U.S. Cl. .............. 526/132; 556/7; 556/8; 556/51; 502/167; 502/200; 526/172

(58) Field of Classification Search .......... 556/7, 556/8, 51; 502/167, 200, 202; 526/134, 526/172, 132
See application file for complete search history.

(56) References Cited

U.S. PATENT DOCUMENTS

| | | | |
|---|---|---|---|
| 4,363,747 A | 12/1982 | Hawthorne et al. | |
| 5,407,884 A | 4/1995 | Turner et al. | |
| 5,483,014 A | 1/1996 | Turner et al. | |
| 5,830,958 A | 11/1998 | Peifer et al. | |
| 6,245,706 B1 | 6/2001 | Hlatky | |

FOREIGN PATENT DOCUMENTS

| | | |
|---|---|---|
| EP | 0 638 593 A1 | 2/1995 |
| JP | 07-070222 | 3/1995 |
| WO | WO 97/10248 | 3/1997 |
| WO | WO 99/05182 | 2/1999 |
| WO | WO 00/75204 A1 | 12/2000 |
| WO | WO 01/00691 | 1/2001 |
| WO | WO 01/16189 A1 | 3/2001 |

OTHER PUBLICATIONS

Crowther et al., "Group 4 metal dicarbollide chemistry, synthesis, structure and reactivity of electrophilic alkyl complexes $(Cp)(C_2B_9H_{11})M(R)$ (M=Hf, Zr)." Journal American Chemical Society, 113:1455-1457, 1991.

Kim et al., "Dicarbollide analogues of the constrained-geometry polymerization catalyst." Organometallics, 20: 4298-4300, 2001.

Wilson et al., "Development of carborane synthons: Synthesis and chemistry of (aminoalkyl) carboranes," Inorganic Chemistry, 31: 1955-1958, 1992.

Zhu et al., "The first half-sandwich d°-metallacarboranes stabilized by metal-nitrogen sigma bond using $C_{(cage)}$-appended anionic alkylamido moiety: a synthetic investigation." Inorganic Chemistry Communications, 4:486-489, 2001.

Zhu et al., "Synthesis and characterization of constrained-geometry half-sandwich sila- and germacarboranes derived from a trianionic $C_{(cage)}$-appended alkyloxo-$C_2B_9$-carborane ligand." Inorganic Chemistry Communications, 5: 296-299, 2002.

Russell N. Grimes, *Carboranes*, New York: Academic Press, 1970, p. 197-198, ISBN 75-127684.

Dodge et al., Titanium and zirconium $Et_2C_2B_4H_4$-Metal-Phosphine complexes: Synthesis, characterization, and ethylene polymerization activity. Journal of the American Chemical Society, 12:10573-10580, 2000.

Kim et al., Dicarbollide analogues of the constrained-geometry polymerization catalyst. Organometallics, 20: 4298-4300, 2001.

Wang et al., Reactions of $L_2Zr(NMe_2)_2$ with $Me_3Al$ and PhC=CH: synthesis and structural charaterization of new zirconium carborane complexes $[L_2=Me_2Si(C_9H_6)(C_2B_{10}H_{10})$ and $Me_2C(C_5H_4)(C_2B_{10}H_{10})]$.Journal of Organometallic Chemistry, 683: 39-43, 2003.

Wang et al., Synthesis, structural characterization, and olefin polymerization behavior of Group 4 metal complexes with constrained-geometry carborane ligands. Organometallics, 20: 5110-5118, 2001.

Wang et al., Multiple insertion of unsaturated molecules into the Zr-N bonds of $[n_:6-Me_2A(C_9H_6)(C_2B_{10}H_{10})]Zr(Nme_2)_2$ (A=C, Si). Organometallics, 22: 4522-4531, 2003.

Zi et al., Synthesis, structural charaterization, and catalytic property of Group 4 metal carborane compounds with a $^iPr_2NB$-bridged constrained-geometry ligand. Organometallics, 21: 3850-3855, 2002.

International Search Report for International Application No. PCT/SG2004/000297.

*Primary Examiner*—Caixia Lu
(74) *Attorney, Agent, or Firm*—Foley & Lardner, LLP (57) ABSTRACT

Disclosed is a Ziegler-Natta catalyst for olefin polymerization comprising a metal cation of Group 4 or 14 of the Periodic Table (IUPAC 1976) that is coordinated to
a. a carborane dianion group;
b. a heteroatom anion, said heteroatom being preferably in the terminal position of a hydrocarbyl bridge comprising at least two carbon atoms, wherein at least one bridging carbon atom may be replaced by Si; and
c. a valence group.

26 Claims, 5 Drawing Sheets

(III)

CARBORANE TRIANION BASED CATALYST

The present invention relates to a Ziegler-Natta type catalyst for olefin polymerization, to the preparation of such catalyst and to the use of this catalyst for polymerizing olefins.

One main focus in research and development in polymer chemistry is to identify new generations of catalysts for polymerization reactions. Ziegler-Natta (ZN) type polyolefin catalysts are well known in the polymer field for a long time for the polymerization of simple olefins to obtain a desired molecular weight. Generally, Ziegler-Natta catalysts comprise (a) at least a catalyst component formed from a transition metal compound of Group 4 to 6 of the Periodic Table (IUPAC, Nomenclature of Inorganic Chemistry, 1976), a metal compound of Group 1 to 3 of the Periodic Table (IUPAC), and, optionally, a compound of group 13 of the Periodic Table (IUPAC) and/or an internal donor compound. ZN catalyst may also comprise (b) further catalyst component(s), such as a co-catalyst and/or an external donor.

A subgenus of such ZN catalysts belongs to the group of metallocenes. Said metallocenes bear generally 1, 2 or 3 organic ligands which are η-bonded to the metal, e.g. a $\eta^{2-6}$-ligand, such as a $\eta^5$-ligand. Preferably, a metallocene is a Group 4 to 6 transition metal, suitably titanocene, zirconocene or hafnocene, which contains at least one $\eta^5$-ligand. Such $\eta^5$-ligand can, for example, be an optionally substituted cyclopentadienyl (Cp), indenyl, tetrahydroindenyl or fluorenyl ligand.

One of the advantages of metallocenes in polymerization has been the fact that they often appear to be "single-site" catalysts that give a narrow range of molecular weight polymers of very similar molecular structure. For example, Peifer et al. describe in U.S. Pat. No. 5,830,958 a process for preparing a polynuclear metallocene, which is useful for using such metallocenes to produce solid prepolymerized metallocene-containing catalysts and for the olefin polymerisation.

The PCT-application WO 97/10248 discloses metallocene compounds with an open-pentadienyl containing radical for the use in catalyst systems for the polymerization of olefins. Polymers that are produced include HDPE, LLDPE, ethylene/propylene/(diene) elastomers and the like.

Other catalysts useful for the preparation of substantially terminally unsaturated polyolefins are described in WO 99/05182 of Dorer et al., Dorer discloses metallocene complexes comprising diketonic, β-ketoesters or triflate anions. Some of the catalysts are suitable for use with co-catalysts to prepare polymers.

While speculations remain concerning the actual structure of the active catalyst species of such ZN metallocenes, it appears as generally accepted that the structure of the catalytically active species is a metal cation in the presence of a labile stabilizing anion, such as anions of the borane type.

Recently, a ionic polymerization catalyst system component comprising a stable and bulky anion containing a plurality of boron atoms has been disclosed by Hlatky in U.S. Pat. No. 6,245,706. Hlatky used several borane or carborane clusters as stable anions.

A related kind of catalysts is disclosed in U.S. Pat. No. 5,407,884. Therein, a cationic metallocene catalyst and a compatible stable, bulky, non-coordinating anion containing a plurality of boron atoms, such as borate, carborate, borane, carborane, metallaborane and metallacarborane compounds are disclosed. The catalyst of U.S. Pat. No. 5,407,884 is useful for the polymerisation of olefins, diolefins and/or acetylenically unsaturated monomers.

Due to the isolobal concept it is possible to replace the Cp⁻-ligand in such metallocenes by the isolobal and isoelectronic dinegative dicarbollide ligand $(C_2B_9H_{11})^{2-}$, either contributing six delocalized π-electrons. As such compounds are isoelectronic with their respective Cp analogues that have been labeled as Ziegler-Natta catalysts, a similar catalytic behavior is expected in the polymerization of olefins.

In U.S. Pat. No. 4,363,747 Hawthorne et al. describe an active carborane 30 catalyst comprising a Group 8 or 9 metal and a carborane dianion. The catalyst is used in hydrogenation, hydroformulation and isomerization reactions.

Crowther et al. describe in J. Am. Chem. Soc. 1991, 113, 1455–1457, the use of such a dicarbollide substituted complex in the polymerization of ethylene while Kang et al. report the polymerization of ethylene with a comparable dicarbollide metal complex (Organometallics 2001, 20, 4298–4300).

Furthermore, Zhu at al. in Inorganic Chemistry Communications 2001, 4, 486–489 describe the first half-sandwich metallacarborane which is stabilized by metal-nitrogen sigma bond using a anionic alkylamido moiety linked to the carborane cage. Finally, Zhu et al. Inorganic Chemistry Communications 2002, 5, 296–299 describe sila- and germacarborane derivatives derived from a trianionic $C_{(cage)}$-appended alkyloxo-$C_2B_9$-carborane ligand.

Up to now, most of the known ZN catalyst systems including the carborane metal complexes failed to produce functionalized polyolefins (e.g., polymers from halogenated olefins) because the early transition metal centers in these catalysts are highly electrophilic which generally makes it impossible to use olefins containing polar functional groups as monomers or co-monomers. Therefore, conventional free radical polymerization is still the current technique used in the polymer industry to produce a wide range of functionalized polymers such as polyvinylacetate, polyvinylchloride or polytetrafluoro-ethylene.

Functionalized polyolefins are of prime interest for industrial organizations because of the low cost of the monomer and their wide range of applications. In fact, the main concern at the production level is the ability to produce and supply a material with the characteristics required by a customer. At the manufacturing scale, the commonly used catalysts do not allow sufficient control over the reaction parameters to manage the production in the expected cost efficient manner. In addition, the mechanistic implications of the free radical method makes this method unsuitable for the preparation of predetermined polymer architectures with precise and narrow molecular weight distributions.

Therefore, there is a need for a new type of ZN catalysts for the polymerization of olefins and/or functionalized olefins to prepare polymers and/or functionalized polymers or co-polymers. There is also the need to provide a ZN catalyst for polymerizing olefins that can lead to precise and narrow molecular weight distributions. Consequently, it is a goal of the present invention to provide a ZN catalyst that fulfills these needs.

This goal is solved, for example, by the Ziegler-Natta (ZN) catalyst and the process for preparing a Ziegler-Natta catalyst as defined in the respective independent claims.

In a first aspect, the invention refers to a Ziegler-Natta catalyst for olefin polymerization of the present invention comprises a metal cation of Group 4 or 14 of the Periodic Table (IUPAC 1976) that is coordinated to a. a carborane dianion group;
b. a heteroatom anion, said heteroatom being preferably in the terminal position of a hydrocarbyl bridge comprising at least two carbon atoms, wherein at least one bridging carbon atom may be replaced by Si; and
c. a valence group.

In a further aspect, the catalyst as disclosed in the application is represented by the general formula $$[(R^1)_n(R^d)_mA(R^2)E]MX \quad (I)$$

wherein:
A is a carborane dianion;
$R^1$ is H, a $C_1$–$C_{12}$-hydrocarbyl aliphatic or aromatic group and n is 0 or 1, said $R^1$ being attached to a carbon atom of A;
$R^d$ is H, a $C_1$–$C_{12}$-hydrocarbyl aliphatic or aromatic group, a halide, an o-alkyl or a n-alkyl group and m is 0 or an integer from 1 to 5, said $R^d$ being attached to a boron atom of A;
$R^2$ is a hydrocarbyl bridge comprising at least two carbon atoms, wherein at least one bridging carbon atom may be replaced by Si;
E is a heteroatom anion of group 15 or 16 of the Periodic Table (IUPAC), which is bridged to A via $R^2$;
M is a fourvalent metal cation selected from the group consisting of titanium, zirconium, hafnium and tin; and
X is a valence group.

As can be taken from formula (I), the metal cation in the catalyst of the instant invention is present in oxidation state of IV+, thereby a stable and neutral metal complex is obtained.

Figure 1:
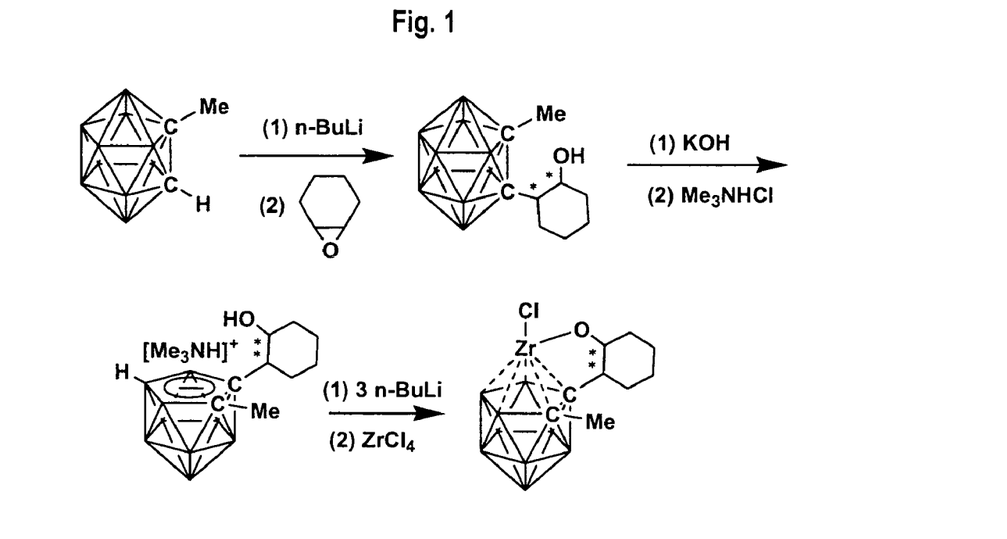
FIG. 1 shows an exemplary preparation route for oxygenic carborane trianion coordinated early transition metal complexes of the present invention from typical icosahedral carborane precursors, wherein 1-Me-1,2-dicarba-closo-dodecacaborane-(12) is used as precursor.

In the above formula (I), A is a (substituted) $C_2B_9H_{10}$ carborane dianion, in particular an open-cage [nido-$C_2B_9H_{10}]^{2-}$ dianion which results by decapitation reaction of [closo-$C_2B_{10}H_{11}$] with an alkaline compound, and further deprotonation with an organic base. The carborane trianion coordinated metal complexes can easily be synthesized in high yields after a two-step process under inert atmosphere followed by chromatography purification from the commercial available carborane starting material as explained below. An explanatory synthesis is shown in FIG. 1 and in Example 1.

In the above formula (I), $R^1$ is selected from the group consisting of substituted or unsubstituted $C_1$–$C_{12}$-hydrocarbyl aliphatic or aromatic group. Examples of suitable aliphatic groups are methyl, ethyl, propyl, isopropyl, butyl, isobutyl. The aliphatic group can further be substituted by an aromatic group such as phenyl, for example. Exemplary aromatic groups that can be used as group $R^1$ are phenyl, toluoyl and naphthyl. The aromatic or aliphatic group is optionally linked to a support, preferably by a polymer chain, wherein said polymer chain can comprise ethylene and/or propylene monomer units. The monomer units of the polymer chain are optionally substituted by $C_1$–$C_{12}$-hydrocarbyl aliphatic or aromatic groups. The support serves to immobilize the ZN catalyst. $R^1$ is a substituent bound to a carbon atom of the carborane cage.

In the above formula (I), $R^d$ is selected from the group consisting of substituted or unsubstituted $C_1$–$C_{12}$-hydrocarbyl aliphatic or aromatic group, a halide, an o-alkyl or an n-alkyl group. Examples of suitable aliphatic groups are methyl, ethyl, propyl, isopropyl, butyl, isobutyl. The aliphatic group can further be substituted by an aromatic group such as phenyl, for example. Exemplary aromatic groups that can be used as group $R^1$ are phenyl, toluoyl and naphthyl. The halide can be selected from fluoride, chloride or bromide. Examples of suitable o-alkyl groups are methoxy, ethoxy, propoxy or butoxy, whereas the n-alkyl group is selected from —NHMe, —N(Me)$_2$, —N(Ethyl)$_2$ or —N(Propyl)$_2$. $R^d$ is a substituent bound to a boron atom of the carborane cage.

In the above formula (I), the hydrocarbyl bridge of $R^2$ can be a straight chain or cyclic moiety (—$WR^a_2$—)$_n$, wherein W is C or Si and may be same or different in a bridge. $R^a$ may also be same or different and can be selected from H, halogen, methyl, ethyl, propyl, butyl or isomers thereof and n is an integer from 2 to 8. The hydrocarbyl chain of $R^2$ in formula (I) can also be part of a ring structure, for example a cyclopentyl, cyclohexyl or cycloheptyl ring. $R^2$ is preferably a constrained chiral center enriched hydrocarbyl bridge having at least one chiral center in the hydrocarbyl bridge. "Chiral center enriched" as used herein means that at least one chiral atom, e.g. a carbon atom, and preferably two chiral atoms are present in the chain between the carborane A and the heteroatom E.

In one embodiment of the present invention $R^2$ is a hydrocarbyl bridge selected from cyclobutyl, cyclopentyl, cyclohexyl, cycloheptyl and cyclooctyl, each being optionally substituted by one or more of H, halogen, methyl, ethyl, propyl, butyl or isomers thereof.

In this connection, it is noted that the length of bridge as used in the present invention with a length of two to eight atoms (n=2 to 8, preferably n=2 to 4) yields very stable metal complexes which in addition show very good catalytic activities in particular over functionalized olefins. This is in contrast to known compounds, e.g. compound 4 of Zhu et al. *Inorganic Chemistry Communications* 2001, 4, 486–489 with n=1 which is instable and moreover does not show appreciable catalytic activity (cf. Example 2)

E is typically selected in formula (I) from a member of the group consisting of N, P, As, Sb, O, S, Se or Te. In some presently preferred embodiments E is N, P or O. In particular, the heteroatom E is a —NR$^3$ or —PR$^3$ anion, wherein $R^3$ is a $C_1$–$C_{12}$-hydrocarbyl aliphatic or aromatic group. E is directly linked to the metal cation M and additionally connected to the carborane cage via $R^2$.

In the above formula (I), X is a valence group saturating the remaining coordination valence of the central metal atom and is selected from the group consisting of halide, pseudohalide, sulfonate, —NR$_m$, wherein R is a lower alkyl group having 1 to 6 carbon atoms or aryl and m is 1 or 2, and a weak-coordinating or non-coordinating anion. The weak coordinating or no-coordinating anion may be a [CB$_{11}$]$^-$, BF$_4^-$, BPh$_4^-$ or a PF$_6^-$ anion.

In one embodiment of the present invention, the Ziegler-Natta catalyst for olefin polymerization comprises a metal cation of Group 4 or 14 of the Periodic Table (IUPAC 1976) wherein the catalyst is represented by the general formula $$[(R^1)_n(R^d)_mA(R^2)E]MX \quad (I)$$

wherein:
A is a $C_2B_9H_{10}$-carborane dianion;
$R^1$ is methyl, ethyl or phenyl and n is 0 or 1, said $R^1$ being attached to a carbon atom of A;
$R^d$ is a halide, an o-alkyl or n-alkyl group, and m is 0 or an integer from 1 to 3, said $R^d$ being attached to a boron atom of A;
$R^2$ is a constrained 5 to 8 membered, chiral center enriched ring having two to four carbon atoms between A and E, at least one of which carbon atoms being chiral, selected from 5 to 8 membered cyclic (—$WR^a_2$—)$_n$, wherein W is C or Si and may be same or different in a bridge, $R^a$ may be same or different and is selected from H, halogen, methyl, ethyl, propyl, butyl or isomers thereof;

E is a heteroatom anion selected from [NR³]⁻ or O⁻, which is bridged to A via R², E being optionally substituted by R³ anion, wherein R³ is a $C_1$–$C_{12}$-hydrocarbyl aliphatic or aromatic group;

M is a fourvalent metal cation selected from the group consisting of titanium, zirconium, hafnium and tin; and X is a valence group.

In another embodiment of the present invention the Ziegler-Natta catalyst for olefin polymerization comprises a metal cation of Group 4 or 14 of the Periodic Table (IUPAC 1976), wherein the catalyst is represented by the general formula $$[(R^1)_n(R^d)_m A(R^2)E]MX \qquad (I)$$

wherein:

A is a $C_2B_9$-carborane dianion;

R¹ is methyl, ethyl or phenyl attached to a carbon atom of A; n is 1;

m is 0;

R² is a cyclohexyl ring having two carbon atoms between A and E;

E is —[NR³]⁻ or —O⁻, wherein R³ is a $C_1$–$C_{12}$-hydrocarbyl aliphatic group, E being bridged to A via R²;

M is a fourvalent metal cation selected from the group consisting of titanium and zirconium; and X is a valence group.

The ZN catalyst of the present invention can be prepared in a process comprising:

a) reacting $[(R^1)_n(R^d)_m(C_2B_9H_{11})]$ with an organic base and an electrophilic reagent that comprises at least two backbone atoms;

b) reacting the compound obtained in a) with an alkali metal hydroxide in the presence of a quaternary ammonium salt; and c) reacting the compound obtained in b) with an organic base and $MXZ_3$;

wherein R¹ is selected from the group consisting of $C_1$–$C_{12}$-hydrocarbyl aliphatic or aromatic group or a polymer chain, optionally linked to a support, preferably a polymer chain, said polymer chain comprising ethylene, propylene monomer units, said units optionally being substituted by $C_1$–$C_{12}$-hydrocarbyl aliphatic or aromatic groups, said support serving to immobilize the ZN catalyst;

$R^d$ is selected from the group consisting of H, a $C_1$–$C_{12}$-hydrocarbyl aliphatic or aromatic group, a halide, an o-alkyl or a n-alkyl group;

M is a fourvalent metal cation of Group 4 or 14 of the Periodic Table (IUPAC 1976) and X is a valence group;

Z is a leaving group selected from halide, sulfonate, or NR'R", wherein R' is hydrogen, alkyl, aryl, alkylaryl or arylalkyl and R" is alkyl, aryl, alkylaryl or arylalkyl;

n is 0 or an integer from 1 to 6.

Figure 9:
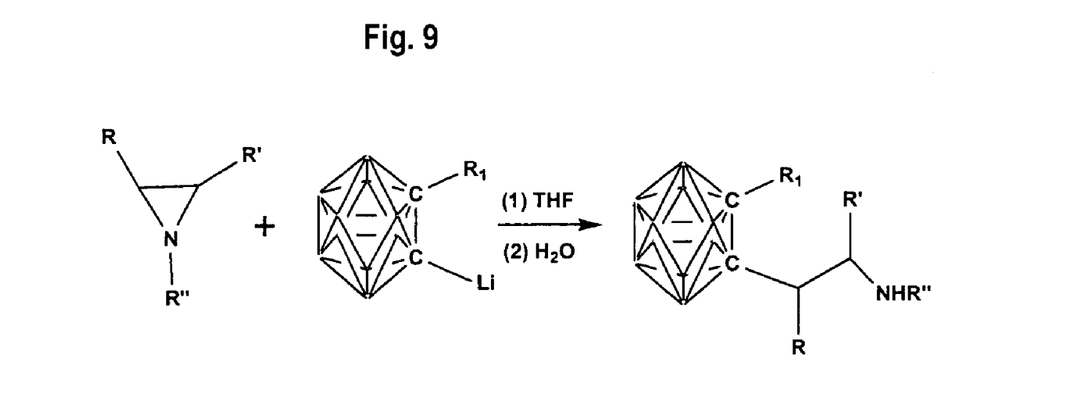
FIG. 9 shows a scheme for reacting an icosahedral carborane precursor with an aziridine as a example for the formation of a hydrocarbyl brigde $R^2$ by reaction of the carborane precursor with an electrophilic reagent that comprises at least two backbone atoms. The substituents R, R' and R" in FIG. 9 may be, for example, any alkyl, aryl, alkylaryl or arylalkyl residue as defined in connection with formula (II) herein.

The electrophilic reagent used in the process provides for at least two of the backbone (main chain) atoms of the hydrocarbyl bridge R². Depending on the size of the bridge that is wanted the electrophilic agent may have 2 to 8 backbone (main chain) atoms. The electrophilic reagent can be a suitable alkyl halide, for example 1-chloro-2-aminoethane, 1-chloro-2-aminopropane, 3-chloropropylamino hydrochloride, methyl 4-iodobutyrate, ethyl-4-chlorobutyrate ethyl 3-chloropropionate, or the like. It can also be a heterocyclic compound such as a substituted or unsubstituted epoxide (for example ethylene oxide, propylene oxide) or a substituted or unsubstituted aziridine. Upon attack by a nucleophile, such a cyclic compound undergoes a ring opening to provide a straight or branched chain hydrocarbyl bridge and, followed by a further deprotonation with a base, can supply a substituted anion such RR"N(−1) or an oxo anion that is suitable for reaction with a compound $MXZ_3$ (cf., FIG. 9). The electrophilic reagent can also be a geometry-constrained (cyclic) compound. A presently preferred class of such electrophilic compounds are 5 to 8 membered cyclic alkenyl oxides such as cyclopentene oxide, cyclohexene oxide or cyclooctene oxide. In case such cyclic alkenyl oxides are used, they are considered as electrophilic reagents that comprises two backbone atoms, namely the ring atoms to which the oxygen atom is bound (cf., FIG. 1 in which the structure of cyclohexene oxide is depicted).

In case, the bridge R² comprises one or more silicon atoms, the electrophilic reagent can a substituted silane of the formula $$Y(CH_2SiMe_2)_n NHR^z \qquad (IIa)$$

wherein in formula (IIa),

Y is halide;

$R^z$ is aryl, alkyl, alkylaryl or arylalkyl; and n is an integer between 1 and 8. Aryl, alkyl, alkylaryl or arylalkyl are used in accordance with the respective definition given below for the residues R' and R".

In presently preferred substituted silanes of formula (IIa) Y is either Cl or Br and n is 1, 2 or 3. One general class of such a substituted silane is $Cl(SiMe_2)_n NHR^z$.

Other substituted silanes that can be used as electrophilic reagents are compounds of the formula $$Y(SiMe_2)_n NHR^z \qquad (IIb),$$

$$Y(CH_2SiMe_2)_n Y \qquad (IIc), \text{ or}$$

$$Y(SiMe_2)_n Y \qquad (IId)$$

wherein Y and n are defined as above for formula (IIa) with the exception that for the compounds of formula (IIb) and (IId) n is an integer from 2 to 8.

In some embodiments of the method, the metal cation of Group 4 or 14 of the Periodic Table (IUPAC 1976) is titanium, zirconium, hafnium or tin.

In case the metal compound $MXZ_3$ comprises a leaving group NR'R", in which at least one of R' and R" is alkyl, aryl, alkylaryl or arylalkyl, the same groups which are used for R¹ above can be used. Thus, alkyl groups R' and R" can be straight chained, branched or cyclic, and optionally substituted. Aryl groups used as R' or R" can also be substituted. Typically, alkyl groups having 1 to 12 carbon atoms and aryl groups having 6 to 14 carbon atoms are used. Suitable alkyl groups comprise methyl, ethyl, propyl, isopropyl, butyl, isobutyl. Exemplary aromatic groups that can be used as group R¹ are phenyl, toluoyl and naphthyl. Accordingly, examples of a alkyl- or aryl amino leavings groups NR'R" are NHMe, $N(Me)_2 N(Ethyl)_2$, $N(Propyl)_2$, $N(Ph)_2$, (Toloyl) etc.

Figure 2:
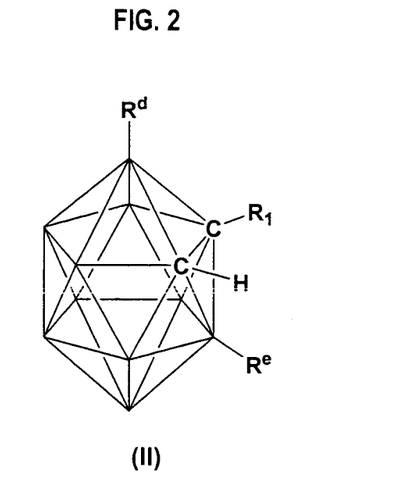
FIG. 2 shows icosahedral carboranes precursors which can be used for the synthesis of the Ziegler-Natta catalyst of the invention.

In more detail, the catalyst of the invention can be prepared from icosahedral carboranes precursors (II) as follows. Such precursors the general formula of which (II) is depicted in FIG. 2, wherein R¹ and $R^d$ are as described above, can be obtained by any method known to the skilled person, for example, by the method described in Inorg. Chem 1992, Vol (No. 10), 1955–1958).

Figure 8:
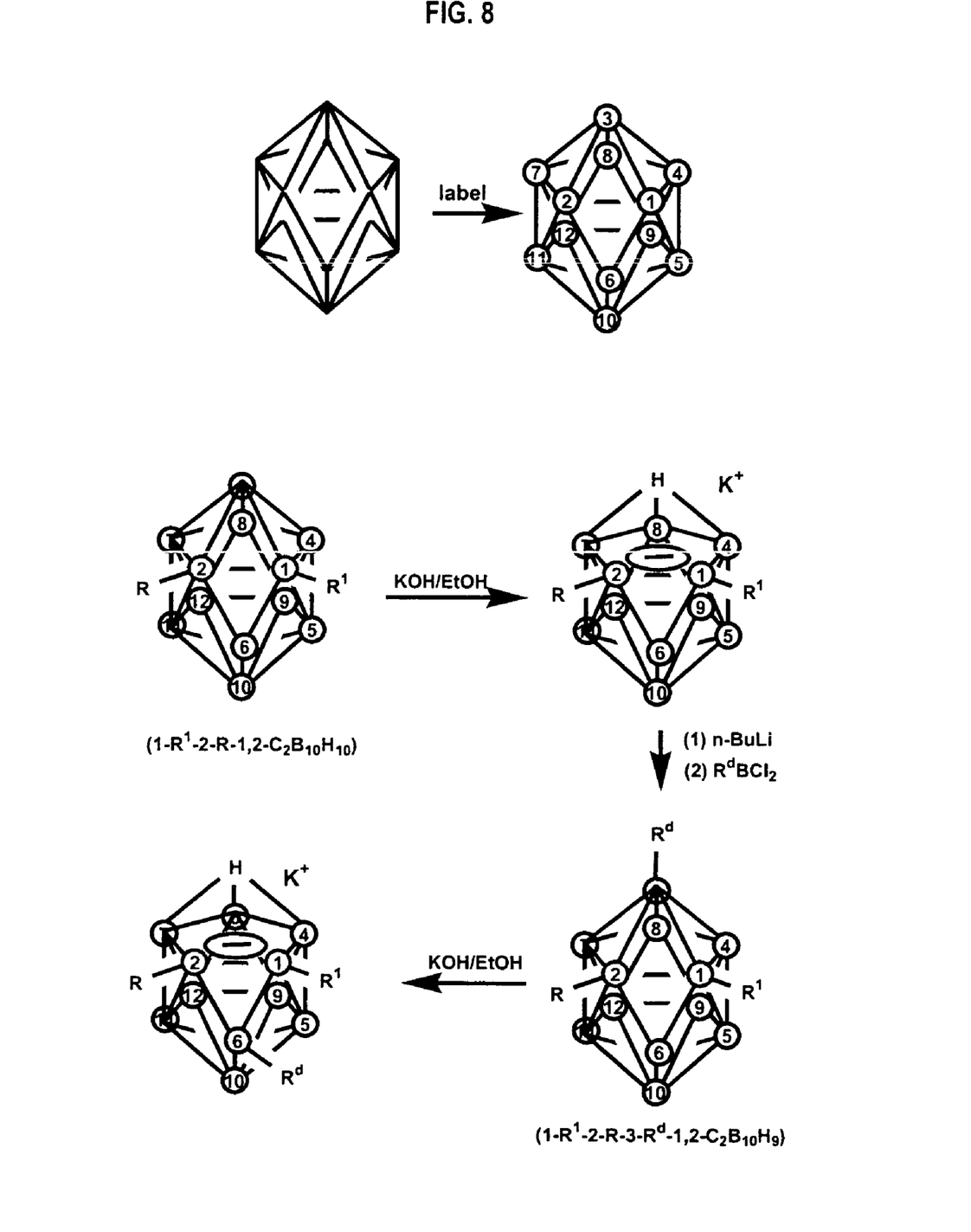
FIG. 8 schematically shows the synthesis of icosahedral carboranes precursors that are useful in the invention and which are substituted at the boron atoms 3 and/or 6 of the carborane cage.

Substitutents can be introduced at the boron atoms of the carborane cage as described on page 197 and 198 (in particular paragraph 9.2) of Carboranes (Russell N. Grimes, Academic Press, New York, 1970, ISBN 75-127684). and the references cited therein, as well as illustrated in FIG. 8. As shown in FIG. 8, after introduction of the substituent $R^1$ at carbon atom 1 of the carborane cage, the resulting 1,2 $C_2B_9H_{10}$-carborane compound can be treated with an organic base and reacted with a compound such as $R^yBCl_2$, wherein $R^y$ is alkyl, aryl, O-alkyl, N-alkyl or halide leading to carborane compounds which are substituted at the 3 and/or the 6 boron atom.

Figure 3:
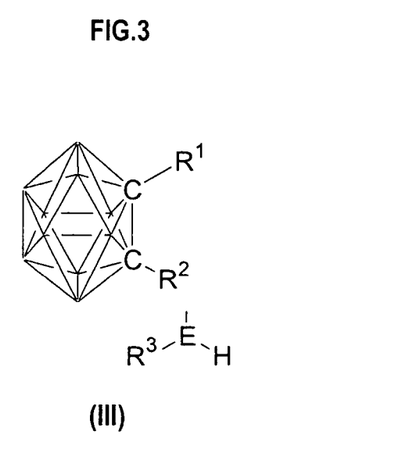
FIG. 3 shows the general formula of the intermediate compound (III) which is obtained in the course of the synthesis of the Ziegler-Natta catalyst of the invention.
Figure 4:
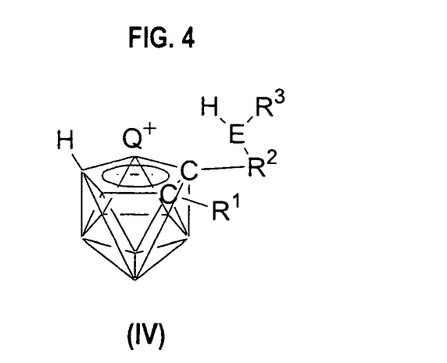
FIG. 4 shows the general formula of the compound (IV) which is obtained in the synthesis of the Ziegler-Natta catalyst of the invention decapitation.
Figure 5:
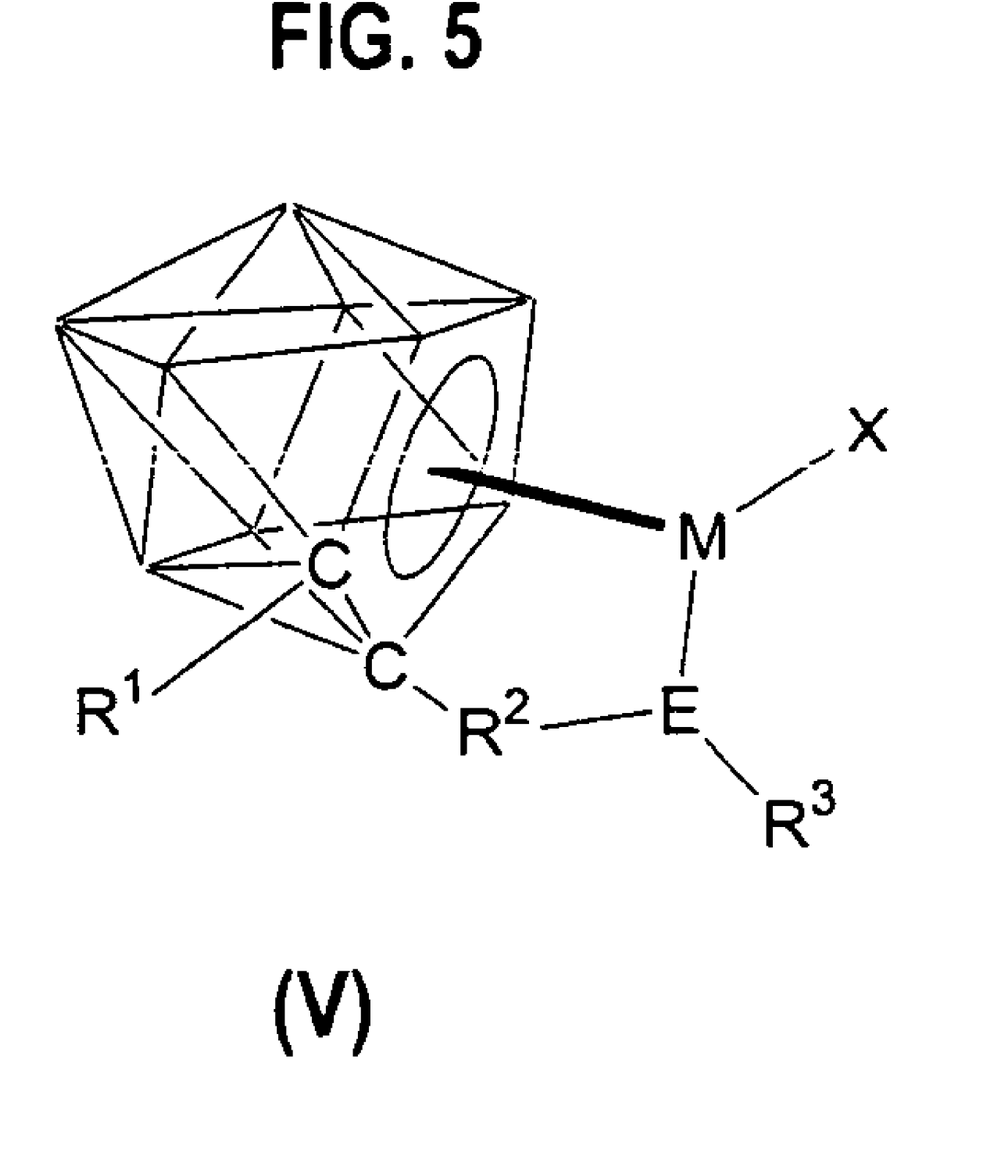
FIG. 5 shows the structural formula of preferred embodiments of the Ziegler-Natta catalyst according to formula (I)

The precursor (II) is preferably treated with an organic base such as n-BuLi, tert-BuLi, PhLi, LDA, followed by reaction with an electrophilic reagent, such as alkylhalides, epoxides, aziridines or geometry-constrained heterocyclic compounds (e.g. cyclohexene oxide), to form the bridge $R^2$. The bridging intermediate is then hydrolyzed into compound (III) which general formula is presented in FIG. 3, wherein E and $R^2$ are as described above. Decapitation reaction of (III) is carried out by alkaline treatment (such as KOH, NaOH, CsF, $Et_3N$ or piperidine) in a polar solvent such as methanol, ethanol, or tetrahydrofurane or any other suitable polar solvent. The resulting species are the open-cage monoanion in which the appended moiety remains intact. The general formula of the synthesized compound (IV) after decapitation is presented in FIG. 4, wherein $Q^+$ is typically the counter ion from the alkaline treatment. Further deprotonation of compound (IV) with an organic base such as n-BuLi, tert-BuLi, or LDA leads to the corresponding trianion which is then combined with the transition metal by addition of, e.g., a halogen salt (Cl or Br) of the metal M to the mixture. This halogen salt of the metal M may also be a monoalkyl or aryl halogen of the metal salt (e.g., $MeMCl_3$, $PhMCl_3$) which can optionally also be substituted by a valence group X as defined above. In an alternative route, compound (IV) is reacted directly with tetrakis(dimethylamino)M (M=as described above) to produce the compounds of the invention. For either method, a pure sample can be obtained by standard purification methods such as recrystallization from any suitable solvent or by chromatographic purification such as silica-gel column chromatography. An example of a suitable solvent is mixture of a $CH_2Cl_2$/n-pentane (1:1) The product of the reaction is a compound of formula (I) as described in FIG. 5.

In the catalyst of the present invention, the carborane cluster [nido-$(R^1)C_2B_9H_{10}$]$^{2-}$ coordinates to a metal cation in an eta($\eta$)-6 fashion by formal donation of six electrons, and thus is a dianionic analogue of commonly used monoanionic Cp-ligand. The use of [nido-$(R^1)C_2B_9H_{10}$]$^{2-}$ cage in place of $Cp^-$ enables the construction of new metal/charge combinative complexes.

The neutral icosahedral carborane cage can be heated to 600° C. without decomposition and its [nido-$(R^1)(R^d)_m C_2B_9H_{10}$]$^{2-}$-cage ions can be recovered unchanged after several hours of heating in solution with aqueous acids and bases. Moreover, the icosahedral carborane cage is resistant to attack by halogenated organic compounds. These properties render the compounds of formula (i) highly suitable for use as catalysts for Ziegler-Natta polymerization of functionalized olefins.

In order to stabilize the metal center, the negative charge heteroatoms are introduced to the coordination moiety which contacts with the carborane cage by a short bridge. This bridge builds up a ring structure in order to stabilize the complex and to provide better catalytic activities. Therefore, formation of 5- to 7-membered rings is preferred in some embodiments. In one of these embodiment, a 6-membered ring is preferably formed, wherein the substituent E is preferably in the 3-position calculated from the carborane dianion.

Figure 6:
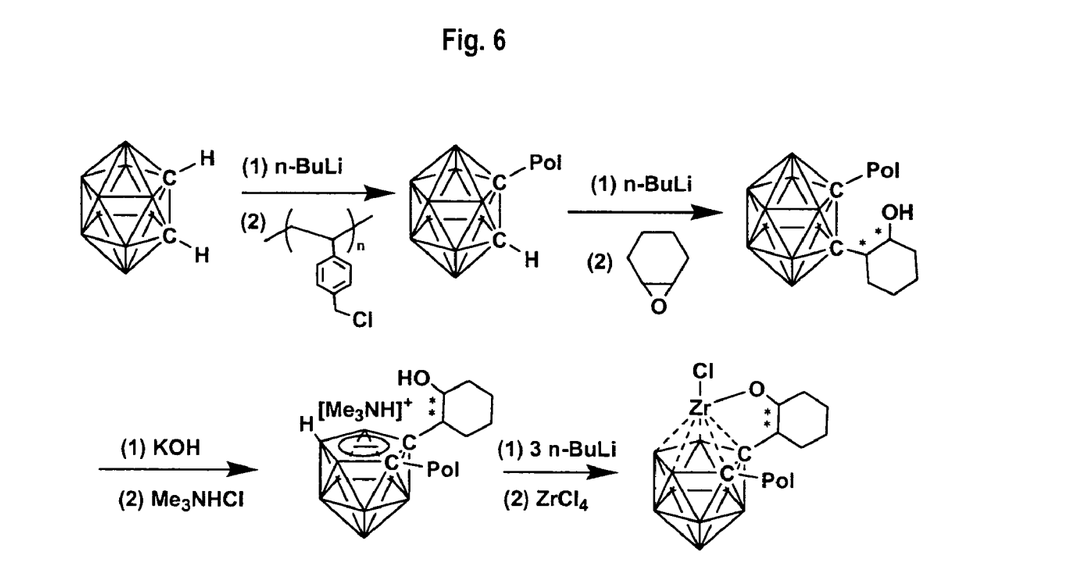
FIG. 6 shows a further preparation method for catalysts of the invention supported on a polymeric support (which is denoted as "Pol" in FIG. 6)
Figure 7:
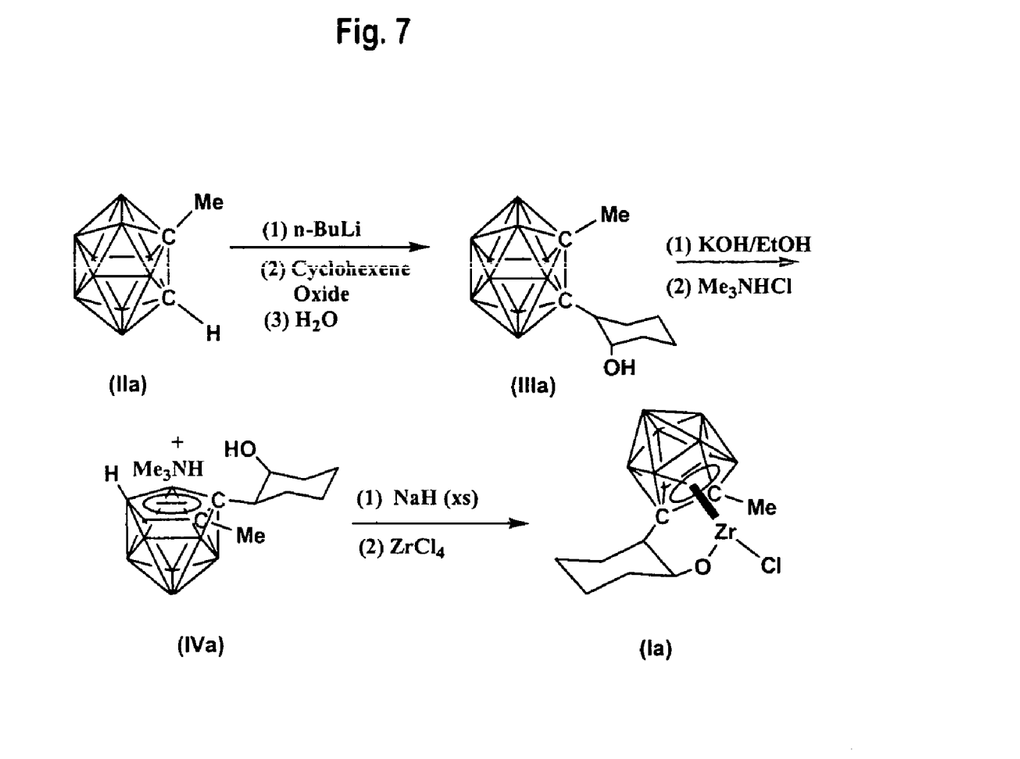
FIG. 7 shows a schematic representation of the synthesis of the Ziegler Natta catalyst (Ia) of the present invention.

In one embodiment of the present invention, the carborane cage and carborane based ZN catalyst may suitably be immobilized on supports by means of a carbon chain which is represented in formula (I) as $R^1$. Supports that can be used for immobilization include organic materials. The organic materials are preferably polymers, such as polyethylene, polypropylene, polystryrene and the like. The so prepared catalyst can be used as a heterogeneous catalyst. It is also referred to an exemplified preparation method as shown in FIG. 6.

It is also possible to use other materials than organic materials as support for immobilizing a Ziegler-Natta catalyst of the invention. Such support materials include inorganic materials such as respective polymers and inorganic metal and non-metal oxides. Examples of suitable materials are macroporous or mesoporous silica or other non-metal or metal-oxide such as alumina, titania or mixtures of oxides. Alternatively, the support may be an in organic polymer. A preferred support is silica.

Independent from the nature of the concrete material used (organic or inorganic), the support can be a porous material. While conventional support materials may be suitable, supports with particular high porosity are advantageous in some embodiments due to their ability to facilitate maximum contact between the reactants and catalyst while retaining the catalyst in supported form.

The compounds of the present invention are active for the polymerization of olefins and/or functionalized olefins without co-catalyst. In particular, polymers can be obtained by a method of polymerizing olefins by reaction of olefins in the presence of a Ziegler-Natta catalyst for olefin polymerization comprising a metal cation of Group 4 or 14 of the Periodic Table (IUPAC 1976) that is coordinated to a. a carborane dianion group;
b. a heteroatom anion, said hetero atom being preferably in the terminal position of a hydrocarbyl bridge comprising at least two carbon atoms, wherein at least one bridging carbon atom may be replaced by Si; and
c. a valence group.

The catalyst used in some embodiments of the method of polymerizing olefins of the present invention is represented by the general formula $$[(R^1)_n(R^d)_m A(R^2)E]MX \qquad (I)$$

as explained above.

The polymerization reaction may be carried out in a any organic solvent that is suitable for this purpose. Examples of suitable commonly used organic solvents are aliphatic hydrocarbons or functionalized hydrocarbons such as toluene, tetrahydrofurane, dimethylformamide, DMSO and acetonitrile. It is however also possible to carry out the polymerisation reaction in a reaction media that is not a common organic solvent. Examples of such reaction media includes ionic liquids (e.g., 1-ethyl-3-methyl-imidazolium chrloride or 1 butyl-3-methyl-imidazolium tetrafluoroborate) which are available from Solvent Innovation GmbH, Cologne, Germany, for example, or perfluorinated solvents such as hexafluorobenzene, perfluorohexanes, or FC-77 (mainly perfluoro-2-butyltetrahydrofuran). It can been seen from polymerization results using a catalyst of the invention that polymers with a relatively narrow molecular weight distribution are generally produced under mild conditions.

These advantages render the catalysts disclosed herein to be especially useful in polymer production, in particular of functionalized polymers.

The catalyst of the invention can be used alone or together with a separate co-catalyst as a Ziegler-Natta catalyst for the (co)-polymerization of an olefin or a functionalized olefin in a manner known in the art. Functionalized olefins are preferably used. It is also possible to combine the catalyst of the invention with one or more other ZN, either known ones or catalysts of the present invention, and/or non-ZN catalysts. The catalyst according to the present invention usually shows good catalytic activities without the use of a co-catalyst such as MAO. Without wishing to be bound to theory, it is believed that the unexpected reactivity of the catalyst of the invention is due to the combination effects of carborane cage and heteroatom, the trianion ligand tightly coordinate with metal center to form a relative stable ring system of 5 to 7 members with an open active site on the transition metal atom for the olefins with functional group.

The olefin to be polymerized using the catalyst system of the invention can be any olefin polymerizable in a coordination polymerization including $C_2$ to $C_{10}$ α-olefins. The polymerization of propylene or ethylene optionally with other α-olefins as co-monomers is also contemplated herein. Suitable co-monomers are $C_2$–$C_{12}$ olefins, preferably $C_4$–$C_{10}$ olefins such, as 1-butene, isobutene, 1-pentene, 1-hexene, 4-methyl-1-pentene, 1-heptene, 1-octene, 1-nonene, 1-decene, as well as dienes such as butadiene, 1,7-octadiene and 1,4-hexadiene, or cyclic olefins, such as norbornene, and any mixtures thereof. In some embodiments, the olefin to be polymerized using the catalyst system of the invention can be a functionalized olefin, wherein the functionalized olefin can be any functionalized olefin known in the art. Suitable functionalized olefins are halogenated olefins or olefins such as vinylacetates, acrylates or styrenes. Enamines also belong to the group of compounds that are advantageously polymerized using the catalyst of the invention. Halogenated olefins comprise vinylchlorid, tetrafluoroethylene etc. Thus, polyolefins and functionalized polyolefins are obtainable using the Ziegler-Natta-catalyst of the present invention.

The quantity of catalyst used will generally depend upon the nature of the catalyst, the reactor types and conditions and the properties desired for the polymer product. Conventional catalyst quantities, such as described in the publications cited herein, may be used.

Furthermore, due to the catalytic activity the prepared polymers have very narrow and precise defined molecular weight distributions making it possible to prepare polymers with predetermined polymer architectures.

In addition, at least one chiral center can be introduced in the molecular geometry in order to control the stereoselectivity of the reaction when preparing the polymers. Preferably, the chiral centers can be incorporated into the bridge that connects the heteroatom to the carborane cage by using a cyclic hydrocarbyl such as cyclobutyl, cyclopentyl, cyclohexyl, cycloheptyl and cyclooctyl as bridging atoms. Other hydrocarbyl groups suitable to introduce a chiral center may also be used.

The polymers prepared by means of the catalyst of the invention can be characterized by use of any conventional method such as GPC, NMR, IR etc.

The invention is further illustrated by reference to the following non-limiting examples and drawings, in which.

EXAMPLES

A preparation route for oxygenic carborane trianion coordinated early transition metal complexes from typical icosehedral carborane precursors (such as 1-Me-1,2-dicarba-closo-dodecacaborane-(12)) (IIa) is shown in FIG. 1 and explained in the following Examples. A further preparation method for catalysts supported on a polymeric support is schematically shown in FIG. 6.

Example 1

(1) Synthesis of IIIa. A solution of 1.00 g (6.32 mmol) of IIa dissolved in a 20 ml dry ethyl ether was cooled to −78° C. and 4.20 ml (6.72 mmol) of n-BuLi (1.6 M in n-hexane) was added under argon. After 30 min of the addition, the mixture was warmed to room temperature spontaneously and continued stirring for 4 h followed by addition of 0.70 ml (6.80 mmol) of cyclohexene oxide with a syringe at 0° C., then the reaction was proceeded at room temperature for another 6 h before hydrolysis with 10 ml water. The organic phase was separated with a separate funnel, and the aqueous phase was extracted with 2×25 ml ethyl ether. After drying with $MgSO_4$, the solvent was removed under reduced pressure and the residue was recrystallized with n-hexane to obtain 1.40 g pure IIIa, yield 86%. M.p. 101–103° C. $^1$HNMR (400 MHz in $CDCl_3$, ppm), δ=3.40 (C$\underline{H}$—O), 1.80 (—C$\underline{H}_3$), 0.63–2.90 (B$\underline{H}$, C$\underline{H}$, O$\underline{H}$). IR (KBr pellet, $cm^{-1}$), 3062(s), 2588(vs), 1447(m), 1390(m), 1229(w), 1133(m), 1094(m), 1017(s), 934(m), 722(s).

(2) Synthesis of IVa. 1.50 g (5.85 mmol) of IIIa was added to a clear solution of 2.00 g (32.08 mmol) potassium hydroxide in 40 ml of 95% ethanol with continuous stirring. After all of the solid dissolved completely, the mixture was heated to reflux for 16 h. The vessel was cooled to room temperature, and the solvent was removed under reduced pressure. Then the sticky residue was dissolved in 20 ml water and neutralized with aqueous HCl. Trimethylamine hydrochloride 1.68 g (17.55 mmol) in 7 ml water was added to the above solution, and a great amount of white solid precipitated. After filtration and drying in vacuum, 1.37 g of solid IVa was obtained, yielded 77%. M.p.>200° C. $^1$HNMR (400 MHz in DMSO, ppm), δ=9.4(N$\underline{H}$), 3.56(O$\underline{H}$), 3.18(C$\underline{H}$—O), 2.52(NC$\underline{H}_3$), 2.00–0.95(B$\underline{H}$), –2.81(B$\underline{H}$). IR (KBr pellet, cm$^{-1}$), 3524(vs), 3040(m), 2931(s), 2857(s), 2497 (vs), 1477(s), 1449(s), 1388(s), 1273(m), 1212(m), 1036 (vs), 978(s), 860(m), 472(m).

(3) Synthesis of Ia. 1.50 g (4.92 mmol) of IVa was dissolved in 75 ml of dry tetrahydrofurane, then the mixture was cooled to 0° C. and 1.18 g (29.52 mmol, 60% dispersion in mineral oil) NaH was added carefully. After addition, the system was warmed to room temperature spontaneously, and kept reacting for 30 min at that temperature, then the mixture was heated to reflux for 3 h under continuous stirring. Complete removal of trimethylamine was achieved by passing a stream of argon over the solution and through the condenser during the final 30 min of the reflux period. Stirring was then stopped and the reaction mixture was allowed to cool to room temperature. When excess sodium hydride had settled, the clear THF solution was decanted under argon to another vessel, the residue was washed with 2×15 ml of dry THF and 1.15 g (4.93 mmol) ZrCl$_4$ was added to the THF solution under argon, the mixture was stirred at room temperature for 72 h at room temperature. After filtration and removal of the solvent under reduced pressure, the residue was recrystallized with a mixture of CH$_2$Cl$_2$/n-pentane (v:v=1:1) to give Ia in 79% yield. $^1$HNMR (400 MHz in DMSO, ppm), δ=3.10 (C$\underline{H}$—O), 1.66 (—C$\underline{H}_3$), –0.43–1.90 (B$\underline{H}$, C$\underline{H}$, O$\underline{H}$). IR (KBr pellet, cm$^{-1}$), 3413(s), 2919(vs), 2851(s), 1637(m), 1457(s), 1305(s), 963 (m), 423(m).

(4) Synthesis of polystyrene supported ortho-Carborane Under argon atmosphere, 0.58 g (4.00 mmol) 1,2-C$_2$B$_{10}$H$_{12}$ were added to a 250 mL two-necked round bottom flask, equipped with a magnetic stirring bar and, 100 ml dry THF was then added to dissolve the carborane compound to give a clear solution. The solution was cooled to –78° C. with liquid nitrogen-isopropanol cold bath, and then 2.7 ml (4.32 mmol) n-BuLi (1.6 M in hexane) were added using a syringe with continuous stirring. After the addition, the mixture was kept reacting at that temperature for 30 minutes followed by warming to room temperature spontaneously and reacted for further 4 hours. The solvents were then removed under reduced pressure, and the residue was washed with n-hexane (2×15 ml). The obtained residue was dissolved into 150 mL THF and Merrifield's peptide resin (1%), 2.0 g (3.94 mmol Cl$^-$), was added and kept stirring at room temperature under argon for two days. At the end of the reaction process, the mixture was heated to reflux for 4 hours before cooling down to room temperature and quenched with 3.0 ml methanol. The solvents were removed under reduced pressure and the crude product was washed with deionized water (2×10 ml) and n-hexane (2×20 ml) to remove any trace of LiCl and starting material 1,2-C$_2$B$_{10}$H$_{12}$, then dried in high vacuum for two days to lead a pale yellow solid 2.40 g polystyrene supported ortho-carborane in 88% yield. The collected aqueous solution was combined and concentrated to 5.0 ml and subjected to titration with AgNO$_3$ to detect the amount of the produced LiCl as 0.15 g. IR (KBr pellet, cm$^{-1}$): 3644, 2952, 2535, 1945, 1872, 1802, 1748, 1703, 1704, 1602, 1583, 1542, 1510, 1490, 1420, 1366, 1267, 1152, 900, 556.

The subsequent synthesis of the catalyst of the invention can then be carried following the synthesis of compound Ia as explained above and as illustrated in FIG. 6.

Example 2

In this example, the catalytic activity of compound Ia is studied using vinyl chloride, (tert)-butyl acrylate, styrene and ethene as polymerizable monomers.

The polymerisation of vinyl chloride catalysed by compound Ia has been proceeded in tetrahydrofurane solvent with the high PVC yield reach to 43.8% without co-catalyst. The polymerization of vinyl chloride also can occur at room temperature in other organic solvents (e.g. toluene, dimethylformamide, DMSO or acetonitrile).

Some polymerization results are summarized in the following Table 1. As can be taken from these results, the catalyst of the present invention yielded a polymer having a well defined molecular weight with a narrow molecular weight distribution. It should further be noted that the catalytic activity for polymerization of ethylene of compound 4 described in Zhu at al. in *Inorganic Chemistry Communications* 2001, 4, 486–489 with co-catalysts MAO is 51 kg PE per mol catalyst per h per 1 bar which shows that the activity of this compound is much lower than that of the catalysts of the present invention. Furthermore, compound Ia is stable and can be handled in air over a sufficiently long period of time (about 13 minutes) and can be stored under inert atmosphere for more than one month whereas compound 4 of Zhu et al. *Inorganic Chemistry Communications* 2001, 4, 486–489 is far more sensitive to air and moisture, in fact it decomposes very fast in air.

TABLE 1

Results of polymerization using compound Ia ($R^2$ = , M = Zr, $R_1$ = Me, E = O, X = Cl)

| Polymer[a] | Activity[b] | $M_w$ (× 10$^3$) g/mol[c] | $M_w/M_n$ |
|---|---|---|---|
| Polyvinyl chloride | 40 | 5.6 | 1.6 |
| Poly-(tert)-butyl acrylate | 35 | 4.2 | 1.6 |
| Polystyrene | 64 | 3.6 | 1.8 |
| Polyethene | 33 | 2.7 | 1.7 |

(a) polymerization conditions: amount of catalyst Ia=2.5× 10$^{-6}$ mol. solvent=toluene, temperature=80° C. (polyvinyl chloride and polyethene), 25° C. (polyacrylate and polystyrene), Pressure=1.2 bar (polyvinyl chloride) and 1.5 bar (polyethene), polymerization time=4 hrs.

(b) Activity=kg polymer per mol catalyst per h per 1 bar.

(c) Molecular weight and molecular weight distribution of the polymers were determined by means of gel-permeation chromatography (GPC: Waters 150C) at 145° C. using 1,2,4-trichlorobenzene as a solvent. The weight average molecular weight and polydispersity index ($M_w$ and $M_w/M_n$, respectively) were calculated on the basis of polystyrene standards.

What is claimed is:

1. A Ziegler-Natta catalyst for olefin production wherein the catalyst is represented by the general formula $$[(R^1)_n(R^d)_m A(R^2)E]MX \qquad (I)$$

wherein:

A is a carborane dianion;

$R^1$ is H, a $C_1$–$C_{12}$-hydrocarbyl aliphatic or aromatic group and n is 0 or 1, said $R^1$ being attached to a carbon atom of A;

$R^d$ is H, a $C_1$–$C_{12}$-hydrocarbyl aliphatic or aromatic group, a halide, an O-alkyl or N-alkyl group and m is 0 or an integer from 1 to 5, said $R^d$ being attached to a boron atom of A;

$R^2$ is a constrained chiral center enriched hydrocarbyl bridge comprising at least two carbon atoms, wherein at least one bridging carbon atom may be replaced by Si;

E is a heteroatom anion of group 15 or 16 of the Periodic Table (IUPAC), which is bridged to A via $R^2$ M is a fourvalent metal cation selected from the group consisting of titanium, zirconium, hafnium and tin; and X is a valence group saturating the remaining coordination valence of the central metal atom.

2. The catalyst according to claim 1, wherein A is a $C_2B_9H_{10}$ carborane dianion.

3. The catalyst according to claim 1, wherein $R^1$ is selected from $C_1$–$C_{12}$-hydrocarbyl aliphatic or $C_1$–$C_{12}$-hydrocarbyl aromatic group, wherein said $C_1$–$C_{12}$-hydrocarbyl aliphatic or $C_1$–$C_{12}$-hydrocarbyl aromatic group is optionally linked to a support.

4. The catalyst according to claim 3, wherein the $C_1$–$C_{12}$-hydrocarbyl aliphatic or $C_1$–$C_{12}$-hydrocarbyl aromatic group is linked to a support by a polymer chain.

5. The catalyst according to claim 4, wherein said polymer chain comprises ethylene or propylene monomer units, wherein said monomer units are optionally substituted by $C_1$–$C_{12}$-hydrocarbyl aliphatic or aromatic groups.

6. The catalyst according to claim 1, wherein $R^2$ is a constrained chiral center enriched hydrocarbyl bridge having at least one chiral center in the hydrocarbyl bridge, selected from straight chain or cyclic $(-WR^a{}_2-)_n$, wherein W is C or Si and may be same or different in a bridge, $R^a$ may be same or different and is selected from H, halogen, methyl, ethyl, propyl, butyl or isomers thereof, and n is an integer from 2 to 8.

7. The catalyst according to claim 1, wherein $R^2$ is a hydrocarbyl bridge selected from the group consisting of cyclobutyl, cyclopentyl, cyclohexyl, cycloheptyl and cyclooctyl, and wherein $R^2$ is optionally substituted by one or more of halogen, methyl, ethyl, propyl, butyl or isomers thereof.

8. The catalyst according to claim 1, wherein the heteroatom E is selected from the group consisting of N, P, As, Sb, O, S, Se and Te.

9. The catalyst according to claim 8, wherein the heteroatom E is selected from the group consisting of N, P and O.

10. The catalyst according to claim 1, wherein the heteroatom E is a —$NR^3$ or —$PR^3$ anion, wherein $R^3$ is a $C_1$–$C_{12}$-hydrocarbyl aliphatic or aromatic group.

11. The catalyst according to claim 1, wherein X is a valence group selected from the group consisting of halide, pseudo-halide, sulfonate, —$NR_m$, wherein R is a lower alkyl group having 1 to 6 carbon atoms or aryl and m is 1 or 2, a weak-coordinating anion and non-coordinating anion.

12. The catalyst according to claim 11, wherein the weak coordinating or non-coordinating anion is selected from the group consisting of $[CB_{11}]^-$, $BF_4^-$, $BPh_4^-$ and $PF_6^-$.

13. A Ziegler-Natta catalyst for olefin polymerization comprising a metal cation of Group 4 or 14 of the Periodic Table (IUPAC 1976), wherein the catalyst is represented by the general formula $$[(R^1)_n(R^d)_m A(R^2)E]MX \qquad (I),$$

wherein:

A is a $C_2B_9H_{10}$-carborane dianion;

$R^1$ is methyl, ethyl or phenyl, and n is 0 or 1, said $R^1$ being attached to a carbon atom of A;

$R^d$ is a halide, an O-alkyl or N-alkyl group, and m is 0 or an integer from 1 to 3, said $R^d$ being attached to a boron atom of A;

$R^2$ is a bridge consisisting of a constrained chiral center enriched ring having two to four carbon atoms between A and E, at least one of which carbon atoms being chiral, said bridge having the formula $(-WR_2)_n$, wherein W is C or Si and may be same or different in the bridge, R may be same or different and is selected from H, halogen, methyl, ethyl, propyl, butyl or isomers thereof and n is an integer from 5 to 8;

E is a heteroatom anion selected from $[NR^3]^-$ or $O^-$, which is bridged to A via $R^2$, E being optionally substituted by $R^3$ anion, wherein $R^3$ is a $C_1$–$C_{12}$-hydrocarbyl aliphatic or aromatic group;

M is a fourvalent metal cation selected from the group consisting of titanium, zirconium, hafnium and tin; and X is a valence group.

14. A Ziegler-Natta catalyst for olefin polymerization comprising a metal cation of Group 4 or 14 of the Periodic Table (IUPAC 1976), wherein the catalyst is represented by the general formula $$[(R^1)_n(R^d)_m A(R^2)E]MX \qquad (I),$$

wherein:

A is a $C_2B_9$-carborane dianion;

$R^1$ is methyl, ethyl or phenyl attached to a carbon atom of A; n is 1;

m is 0;

$R_2$ is a cyclohexyl ring having two carbon atoms between A and E;

E is —$[NR^3]$— or —$O^-$; wherein $R^3$ is a $C_1$–$C_{12}$-hydrocarbyl aliphatic group, E being bridged to A via $R^2$;

M is a fourvalent metal cation selected from the group consisting of titanium and zirconium; and X is a valence group.

15. A process for preparing a Ziegler-Natta catalyst for olefin polymerization comprising:

a) reacting $[(R^1)_n(R^d)_m(C_2B_9H_{11})]$ with an organic base, and an electrophilic compound comprising at least two backbone atoms;

b) reacting the compound obtained in a) with an alkali metal hydroxide in the presence of a quaternary ammonium salt; and c) reacting the compound obtained in b) with an organic base and $MXZ_3$;

wherein $R^1$ is selected from the group consisting of $C_1$–$C_{12}$-hydrocarbyl aliphatic group, $C_1$–$C_{12}$-aromatic group and a polymer chain, optionally linked to a support, preferably a polymer chain, said polymer chain comprising ethylene, propylene monomer units, said unit optionally being substituted by $C_1$–$C_{12}$-hydrocarbyl aliphatic or aromatic groups, said support serving to immobilize the ZN catalyst;

R$^d$ is selected from the group consisting of H, a C$_1$–C$_{12}$-hydrocarbyl aliphatic group, C$_1$–C$_{12}$-hydrocarbyl aromatic group, a halide, an O-alkyl group and N-alkyl group;

at least one of the backbone atoms is a chiral center;

M is a fourvalent metal cation of Group 4 or 14 of the Periodic Table (IUPAC 1976) and X is a valence group saturating the remaining coordination valence of the central metal atom;

Z is a leaving group selected from halide, sulfonate, or NR'R", wherein R' is hydrogen, alkyl, aryl, alkylaryl or arylalkyl and R" is alkyl, aryl, alkylazyl or arylakyl.

16. The method according to claim 15, wherein the electrophilic reagent is an alkyl halide.

17. The method according to claim 15, wherein the electrophilic reagent is an 5 to 8 membered cyclic alkenyl oxide.

18. The method according to claim 15, wherein the fourvalent metal cation is selected from the group consisting of titanium, zirconium, hafnium and tin.

19. A method of polymerizing olefins comprising reacting olefin monomers or mixtures thereof in the presence of a Ziegler-Natta catalyst for olefin polymerization wherein the catalyst is represented by the general formula $$[(R^1)_n(R^d)_mA(R^2)E]MX \quad (I)$$

wherein:

A is a carborane dianion;

R$^1$ is a H, C$_1$–C$_{12}$-hydrocarbyl aliphatic or aromatic group and n is 0 or 1, said R$^1$ being attached to a carbon atom of A;

R$^d$ is H, a C$_1$–C$_{12}$-hydrocarbyl aliphatic or aromatic group, a halide, an O-alkyl or N-alkyl group and m is 0 or an integer from 1 to 5, said R$^d$ being attached to a boron atom of A;

R$^2$ is a constrained chiral center enriched hydrocarbyl bridge comprising at least two carbon atoms, wherein at least one bridging carbon atom may be replaced by Si;

E is a heteroatom anion of group 15 or 16 of the Periodic Table (IUPAC), which is bridged to A via R$^2$;

M is a fourvalent metal cation selected from the group consisting of titanium, zirconium, hafnium and tin; and X is a valence group saturating the remaining coordination valence of the central metal atom.

20. The method according to claim 19, wherein said olefin monomers are functionalized by being substituted by a member selected from the group consisting of alkyl, oxyalkyl, halogen, carboxylic acid group, aryl, and substituted aryl.

21. The method according to claim 20, wherein said functionalized olefins monomers are halogenated olefins monomers.

22. The method according to claim 21, wherein said halogenated olefin monomer comprises vinylchlorid and tetrafluoroethylene.

23. The method according to claim 20, wherein said olefin monomers are selected from the group consisting of vinylacetates, acrylates, styrenes and enamines.

24. A method for preparing a Ziegler-Natta catalyst for olefin polymerizations, wherein the catalyst is represented by the general formula $$[(R^1)_n(R^d)_mA(R^2)E]MX$$

comprising:

a) reacting $[(R^1)_n(R^d)_mA]$ with an organic base, and an electrophilic compound comprising the moiety (R$^2$)E;

b) reacting the compound obtained in (a) with an alkali metal hydroxide in the presence of a quaternary ammonium salt; and c) reacting the compound obtained in (b) with an organic base and MXZ$_3$; wherein A is a carborane dianion;

R$^1$ is H, a C$_1$–C$_{12}$-hydrocarbyl aliphatic or aromatic group and n is 0 or 1, said R$^1$ being attached to a carbon atom of A;

R$^d$ is H, a C$_1$–C$_{12}$-hydrocarbyl aliphatic or aromatic group, a halide, an O-alkyl or a N-alkyl group and m is 0 or an integer from 1 to 5, said R$^d$ being attached to a boron atom of A;

R$^2$ is a constrained chiral center enriched hydrocarbyl bridge comprising at least two carbon atoms, wherein at least one bridging carbon atom may be replaced by Si;

E is a heteroatom anion of group 15 or 16 of the Periodic Table (IUPAC), which is bridged to A via R$^2$;

M is a fourvalent metal cation selected from the group consisting of titanium, zirconium, hafnium and tin;

X is a valence group saturating the remaining coordination valence of the central metal atom; and Z is a leaving group selected from halide, sulfonate, and NR'R", wherein R' is H, alkyl, aryl, alkylaryl or arylalkyl and R" is alkyl, aryl, alkylaryl or arylalkyl.

25. The method according to claim 24, wherein A is a C$_2$–B$_9$H$_{10}$ carborane dianion.

26. The method according to claim 24, wherein said electrophilic compound is a 5 to 8 membered cyclic alkenyl oxide.

* * * * *

UNITED STATES PATENT AND TRADEMARK OFFICE
CERTIFICATE OF CORRECTION

PATENT NO. : 7,053,158 B2 Page 1 of 1
APPLICATION NO. : 10/668850
DATED : May 30, 2006
INVENTOR(S) : Zhu, Yinghuai

It is certified that error appears in the above-identified patent and that said Letters Patent is hereby corrected as shown below:

On title page item under "(75) Inventor." Change "Ayer Rajah Crescent" to --Singapore--

Signed and Sealed this

Fifteenth Day of August, 2006

JON W. DUDAS
*Director of the United States Patent and Trademark Office*